United States Patent [19]
Shino

[11] Patent Number: 6,117,139
[45] Date of Patent: Sep. 12, 2000

[54] LIGAMENT GRAFT-SECURING DEVICE

[75] Inventor: Konsei Shino, Osaka, Japan

[73] Assignee: Nagoya Screw Mfg., Co., Ltd., Nagoya, Japan

[21] Appl. No.: 09/345,731

[22] Filed: Jul. 1, 1999

[30] Foreign Application Priority Data

Dec. 25, 1998 [JP] Japan ................................. 10-376770

[51] Int. Cl.[7] ................................. A61F 5/00; A61F 2/30
[52] U.S. Cl. ................................. 606/86; 606/73
[58] Field of Search ................................. 606/69, 65, 71, 606/72, 73, 139, 232, 86, 88, 89, 75, 76; 623/13

[56] References Cited

U.S. PATENT DOCUMENTS 5,314,427 5/1994 Goble et al. ................................. 606/72
5,707,395 1/1998 Li ................................. 606/232

*Primary Examiner*—Michael Buiz
*Assistant Examiner*—(Vikki) Hoa B. Trinh
*Attorney, Agent, or Firm*—Burns, Doane, Swecker & Mathis, LLP

[57] ABSTRACT

A ligament graft-securing device includes a body part; a knotting hole for knotting therein threads sewed to an end of the ligament graft and which is formed at one end of the body part; a through-hole for securing a tensile force-applying thread thereto and which is formed at the other end of the body part; spikes for temporarily fixing the ligament graft-securing device to a bone and which projects from one surface of the body part; and a screw securing hole for securing the ligament graft-securing device to the bone and which is formed on the body part.

12 Claims, 11 Drawing Sheets

LIGAMENT GRAFT-SECURING DEVICE

BACKGROUND OF THE INVENTION

The present invention relates to a device which is used in an operation of securing a soft tissue graft such as tendon or fascia (hereinafter referred to as ligament graft) to bone easily and reliably.

In recent years, in a case where the ligament is torn or damaged in such an extent that it cannot be repaired, an operation of replacing the non-functioning ligament with the ligament graft consisting of tendon or fascia is widely performed. The method of securing the ligament graft to the bone is different according to the length of the ligament graft:

(1) In the case where the ligament graft is not long enough for its one end to emerge from a bone tunnel, threads sewed to the end of the ligament graft is tied around a screw post inserted into the bone in the neighborhood of the tunnel exit or the thread is tied over a button.

(2) In the case where the ligament graft is long enough for its one end to emerge from the bone tunnel exit, the ligament graft is secured to the bone with either a staple or a spike-washer and a screw.

However, in the case of (1), it is difficult to adjust the amount of a tensile force to be applied to the ligament graft. Further, because the threads are tied around the screw or over the button under a high tensile load, the threads are not infrequently broken or loosened. In the case of (2), the ligament graft-securing device is superimposed on the ligament graft on the bony surface, thus projecting to the skin in a very large amount. Consequently, a patient may ache. Finally, the use of the ligament graft-securing device may cause the ligament graft damage because the high compressive and/or impact load is applied thereto. Thus, the ligament grafts are secured to the bone in a various degree of strength.

It is an object of the present invention to solve the above-described problems and provide a ligament graft-securing device capable of securing an end of a ligament graft to bone easily and firmly in a short period of time, with a desired amount of a tensile force being applied to the ligament graft.

SUMMARY OF THE INVENTION

The object of this invention is to provide a ligament graft-securing device for securing a ligament graft having a length not projecting from a bone tunnel formed in a region to which said graft is to be secured which comprises a body part; a knotting hole for knotting therein a thread sewed to an end of said graft and which is formed at one end of said body part; a through-hole for securing a tensile force-applying thread thereto and which is formed at the other end of said body part; a spike for temporarily fixing said graft-securing device to a bone and which projects from one surface of said body part; and a screw securing hole for securing said graft-securing device to said bone and which is formed on said body part.

The object of this invention is to provide a ligament graft-securing device for securing a ligament graft having a length projecting from a bone tunnel formed in a region to which said graft is to be secured which comprises a screw securing hole-forming part having a screw securing hole through which a thread sewed to an end of said graft is inserted and which is used to secure said graft-securing device to a bone and; a flat plate part; a plurality of ligament penetration spikes projecting substantially perpendicularly from said flat plate part; and a plurality of temporarily securing spikes for temporarily securing said graft-securing device to the bone and which are formed on a periphery of said flat plate part such that said temporarily securing spikes project from said flat plate part in substantially parallel with said ligament penetration spikes and in the same direction as that in which said ligament penetration spikes project.

DETAILED DESCRIPTION OF THE PREFERRED EMBODIMENTS

Figure 1:
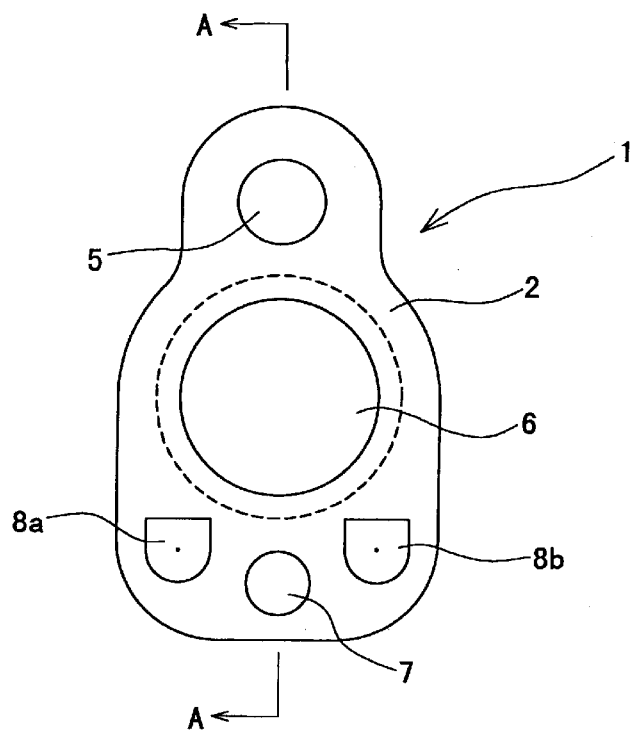
FIG. 1 is a plain view showing a ligament graft-securing device according to an embodiment of the present invention.

A ligament graft-securing device according to an embodiment of the present invention will be described below with reference to FIGS. 1 through 3.

A ligament graft-securing device 1 of the embodiment of the present invention is used to secure to bone a ligament graft of insufficient length to emerge from a bone tunnel exit. The ligament graft-securing device 1 includes a body part 2; a suture hole 5 formed at one end of the body part 2 to knot therein threads sewed to an end of the ligament graft; a through-hole 7 formed at the other end of the body part 2 to pass a tensile force-applying thread thereto; spikes 8a and 8b projecting from one surface of the body part 2 to temporarily fix or secure the ligament graft-securing device 1 to bone; and a screw securing hole 6 formed on the body part 2 to secure the ligament graft-securing device 1 to the bone.

Figure 10:
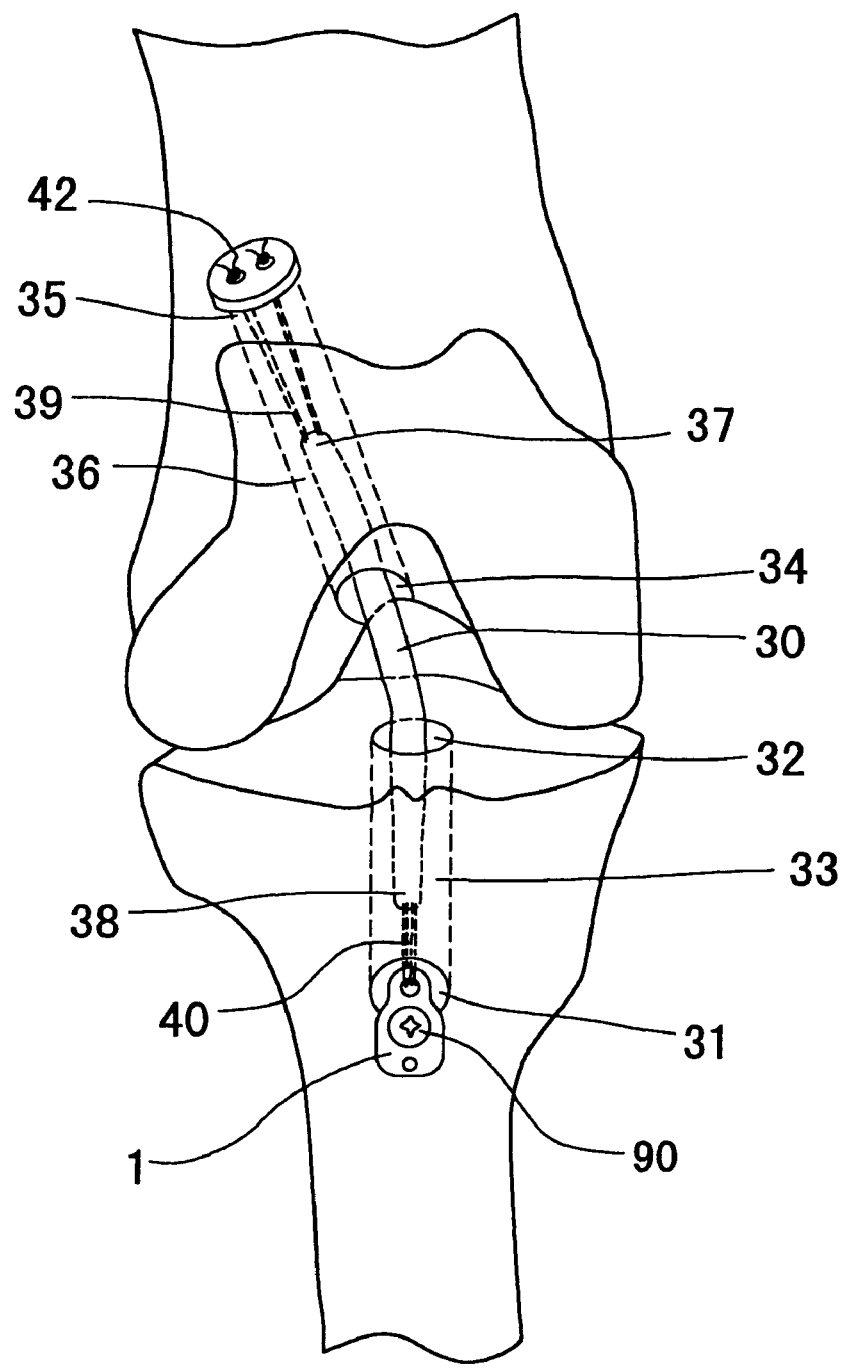
FIG. 10 is an explanatory view for explaining the operation of a ligament graft-securing device according to an embodiment of the present invention.

The body part 2 is almost flat plate-shaped and has the suture hole 5 formed near one end thereof. The ligament graft-securing device 1 is used, with the suture hole 5 positioned at the side of the bone tunnel, as shown in FIG. 10. The spikes 8a and 8b and the through-hole 7 used to fix the tensile force-applying thread thereto are formed near the other end of the body part 2. The screw securing hole 6 is formed between the suture hole 5 and the through-hole 7.

The ligament graft-securing device 1 has a thickness of 1–3 mm and a length of 10–30 mm, preferably 18–30 mm; a width of 6–8 mm and a length of 5–8 mm, preferably 6–30 mm in one side (at the part where the suture hole 5 is formed) thereof; and a width of 5–15 mm, preferably 8–15 mm, more preferably 8–12 mm in the part where the screw securing hole 6 is formed and in the part where the through-hole 7 is formed.

The shape of the ligament graft-securing device 1 is not limited to a specific one but can be selected as desired so long as the ligament graft-securing device 1 does not irritate or damage skin, subcutaneous tissue, muscle when it is implanted inside an organism (human body). For example, as shown in FIGS. 1 and 2, it is preferable that the ligament graft-securing device 1 is rounded. It is preferable that as described above, the periphery of the ligament graft-securing device 1 is also rounded so that it does not irritate or damage skin, subcutaneous tissue and the like.

As the material of the ligament graft-securing device 1, it is possible to use those having a necessary degree of strength and being adaptable for organisms. For example, it is possible to use stainless steel (SUS304, SUS316, and the like of JISG4303), pure titanium (JISH4670), and a titanium alloy (Ti-6Al4V, ASTM F-136 Ti-6Al-4V ELI of JISH4657).

A sewing thread sewed to an end of the ligament graft is knotted in the knotting hole 5. Thus, it is preferable that the knotting hole 5 does not have such a shape as to damage the sewing thread easily, while a high degree of a tensile force is being applied to the sewing thread knotted through the knotting hole 5. Thus, the knotting hole 5 is favorably circular or elliptical and more favorably circular, as shown in FIG. 1. It is favorable that the periphery of the knotting hole 5 does not have such a shape as to damage the sewing thread easily. Thus, as shown in FIG. 3, it is favorable that the periphery of the knotting hole 5 is rounded. Favorably, the knotting hole 5 has a diameter of 2–4 mm and more favorably 3 mm if it is circular.

The two spikes 8a and 8b are formed near either end of the other side (through-hole side) of the body part 2 such that they are parallel with each other and substantially perpendicular to the body part 2. The ligament graft-securing device 1 can be fixed to the bone stably by the spikes 8a and 8b formed thereon. The spikes 8a and 8b are used to temporarily secure the ligament graft-securing device 1, with a desired degree of a tensile force applied to the ligament graft. As shown in FIGS. 2 and 3, each of the spikes 8a and 8b is constructed of a front end part 81 and a base part 82. Preferably, the length of each of the spikes 8a and 8b is 5–10 mm. The number of the spikes 8a and 8b may be two or more or one so long as it can easily secure the ligament graft-securing device 1 to the bone.

Each front end part 81 of the spikes 8a and 8b is preferably pointed so that it can pierce the bone easily. For example, favorably, each front end part 81 is conic, triangular pyramidal, quadrangular pyramidal or the like and more favorably, conic. When the front end part 81 is conic, it is preferable that the angle at the front end of a circular cone is 45–75°. It is favorable that the front end part 81 has a diameter of 2–3 mm. It is more favorable that the front end part 81 has a diameter of 2.5 mm. It is favorable that the front end part 81 has a length of 2–4 mm. It is more favorable that the front end part 81 has a length of 3 mm.

It is preferable that each base part 82 of the spikes 8a and 8b is in the shape of a column, a trigonal prism, a square pole or the like. It is preferable that the base part 82 at the side of the knotting hole 5 is flat, as shown in FIG. 1 to prevent the spikes 8a and 8b from being removed easily from the bone by a force applied thereto from a tensile force application side. It is preferable that the base part 82 has a diameter of 2–4 mm and a length of 5–10 mm when it is columnar.

It is not dispensable that each of the spikes 8a and 8b is constructed of the front end part 81 and the base part 82 but may be tapered from its rear end to its front end.

As the material of the spikes 8a and 8b, it is possible to use a material having a necessary degree of strength and being adaptable for organisms (human body). For example, it is possible to use stainless steel (SUS304, SUS316, and the like of JISG4303), pure titanium (JISH4670), and a titanium alloy (Ti-6Al-4V, ASTM F-136 Ti-6Al-4V ELI of JISH4657). The spikes 8a and 8b may be formed integrally with the body part 2 of the ligament graft-securing device 1 or separately therefrom, provided that the portion where the spikes 8a and 8b and the body part 2 are connected with each other keeps a necessary degree of strength. When the spikes 8a and 8b are formed separately from the body part 2, they are connected with the body part 2 by soldering them to the body part 2 or fitting them into holes formed in the body part 2.

The through-hole 7 is used to fix thereto the sewing thread which is used to continuously apply a desired degree of tensile force to the end of the ligament graft. The through-hole 7 is arranged near or in a middle part of two spikes 8a, 8b (between spikes 8a and 8b). It is favorable that the through-hole 7 is rounded as in the case of the knotting hole 5. Thus, as shown in FIG. 1, it is favorable that the through-hole 7 is circular. It is preferable that the periphery of the through-hole 7 is also rounded for the reason described on the knotting hole 5. When the through-hole 7 is circular, it is favorable that the through-hole 7 has a diameter of 2–4 mm and more favorable that it has a diameter of 3 mm.

The screw securing hole 6 is used to complete the securing of the ligament graft-securing device 1 to the bone in an operation. The screw securing hole 6 is arranged in a middle part between the knotting hole 5 and the through-hole 7. Preferably, the screw securing hole 6 is circular because a screw is used to secure the ligament graft-securing device 1 to the bone. As shown in FIG. 3, preferably, the screw securing hole 6 has the shape of a screw head to prevent the screw head from projecting from the body part 2 in securing the ligament graft-securing device 1 to the bone. In other words, the screw securing hole 6 has a screw head receiving portion for receiving the screw head of the screw 90. In this manner, the skin or the like is prevented from being damaged by the screw head. It is favorable that the screw securing hole 6 has a diameter of 3–8 mm and more favorable that it has a diameter of 4–7 mm. It is favorable that the screw head has a diameter of 4–9 mm, preferably 5–9 mm and more favorable that it has a diameter of 7 mm.

As shown in FIG. 1, in the ligament graft-securing device 1, the knotting hole 5, the screw securing hole 6, the through-hole 7, and the spikes 8a and 8b are on the same plane. The ligament graft-securing device 1 of the present invention is intended to fix the ligament graft to the surface of the bone. Thus, it is preferable that the ligament graft-securing device 1 is so formed that a part thereof does not project into the skin. Preferably, the knotting hole 5 and the through-hole 7 are in a straight line to allow a desired degree of force to be appropriately applied to the ligament graft.

A ligament graft-securing device according to another embodiment of the present invention will be described below.

Figure 4:
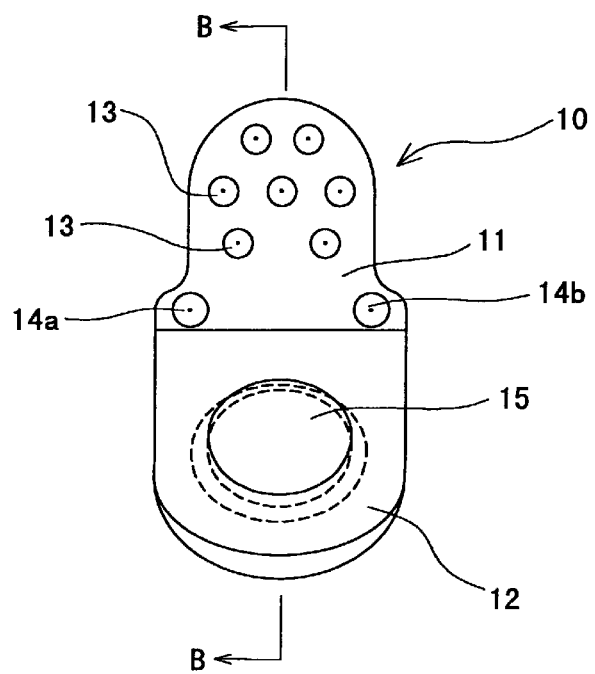
FIG. 4 is a plain view showing a ligament graft-securing device according to another embodiment of the present invention.
Figure 5:
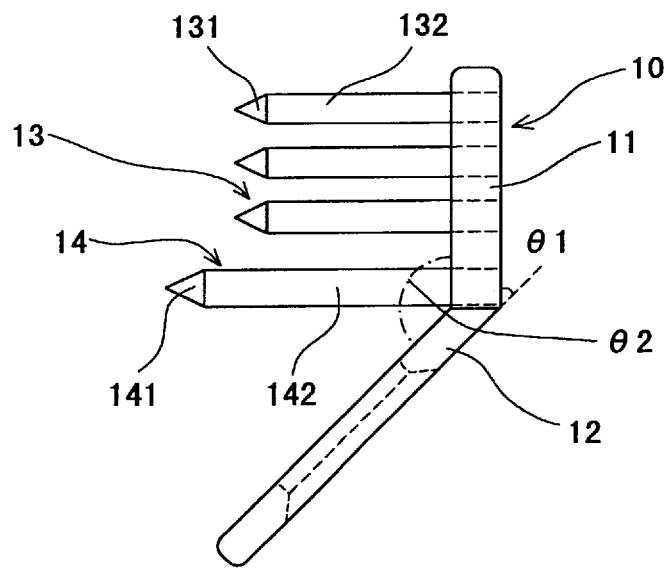
FIG. 5 is a side view showing the ligament graft-securing device shown in FIG. 4.
Figure 6:
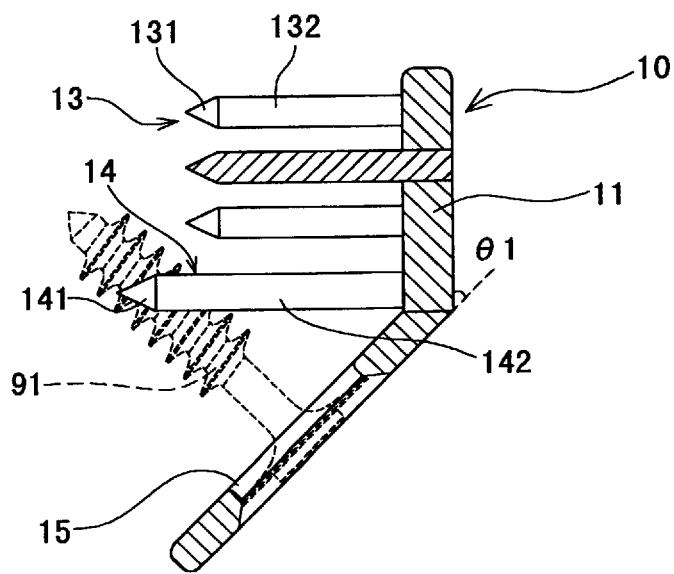
FIG. 6 is a sectional view showing the ligament graft-securing device shown in FIG. 4 taken along a line B—B.

FIG. 4 is a plain view showing the ligament graft-securing device 10 according to another embodiment of the present invention. FIG. 5 is a side view showing the ligament graft-securing device 10 shown in FIG. 4. FIG. 6 is a sectional view showing the ligament graft-securing device 10 shown in FIG. 4 taken along a line B—B of FIG. 4.

A ligament graft-securing device 10 of the embodiment of the present invention is used to secure a bone a ligament. Ligament graft having a length emerging sufficiently from a bone tunnel exit formed in a region to which the ligament graft is to be secured. The ligament graft-securing device 10 includes a screw securing hole-forming part 12 having a screw securing hole 15 through which threads sewed to an end of the ligament graft is passed and which is used to secure the ligament graft-securing device 10 to a bone; a flat plate part 11 located closer to a bone tunnel than the screw securing hole-forming part 12; a plurality of ligament graft penetration spikes 13 projecting substantially perpendicularly from the flat plate part 11; and temporarily securing spikes 14a and 14b which are formed on a periphery of the flat plate part 11 such that they project from the flat plate part 11 in substantially parallel with the ligament graft penetration spikes 13 and in the same direction as the direction in which the ligament graft penetration spikes 13 project and which are used to temporarily secure the ligament graft-securing device 10 to the bone.

In the ligament graft-securing device 10 of the embodiment, an angle is formed between the screw securing hole-forming part 12 and the flat plate part 11 along the bone. The ligament graft-securing device 10 is a bent type ligament graft-securing device. More specifically, the angle (θ1) between the screw securing hole-forming part 12 and the flat plate part 11 is about 45°. More specifically, the angle (θ2) between the screw securing hole-forming part 12 and the flat plate part 11 is about 135°. The angle (θ1) to be formed between the screw securing hole-forming part 12 and the flat plate part 11 is preferably in the range of 0–60° (0–60° expressed by internal angle), for example 30–60°, although the angle (θ1) is different according to the shape of a bone to which the ligament graft is to be secured. The angle (θ2) to be formed between the screw securing hole-forming part 12 and the flat plate part 11 is preferably in the range of 110–180°, more preferably in the range of 100–160°, most preferably in the range of 110–150°, although the angle (θ2) is different according to the shape of a bone to which the ligament graft is to be secured. By setting the angle (θ1 or θ2) to this range, the end of the ligament graft can be secured to the bone tunnel with the spikes 13 and the temporarily securing 14a and 14b. Unlike the method of fixing the end of the ligament graft to the surface of the bone, according to the method of the present invention, it is possible to prevent a patient from aching because the ligament graft and the ligament graft-securing device 10 are not superimposed on each other.

The shape of the ligament graft-securing device 10 is not limited to a specific one but can be selected as desired so long as the ligament graft-securing device 10 does not damage skin, muscle, the surface of a bone tunnel when the ligament graft-securing device 10 is passed through an organism (human body) and fixed to the bone. For example, as shown in FIGS. 4 and 5, it is preferable that the ligament graft-securing device 10 is rounded. It is preferable that as described above, the periphery of the ligament graft-securing device 10 is rounded so that it does not damage the surface of the bone tunnel and the like.

It is preferable that the ligament graft-securing device 10 has a thickness of 1–3 mm; the flat plate part 11 has a width of 6–10 mm and a length of 6–12 m, preferably 6–10 mm; and the screw securing hole-forming part 12 has a width of 8–13 mm, preferably 9–13 mm and a length of 8–13 mm, preferably 8–12 mm.

As the material of the ligament graft-securing device 10, it is possible to use a material having a necessary degree of strength and being adaptable for organisms. For example, it is possible to use stainless steel (SUS304, SUS316, and the like of JISG4303), pure titanium (JISH4670), and a titanium alloy (Ti-6Al-4V, ASTM F-136 Ti-6Al-4V ELI of JISH4657). Of the above materials, a titanium alloy of Ti-6Al-4V is more favorable than the other materials.

A plurality of the ligament graft penetration spikes 13 are projected substantially perpendicularly to the flat plate part 11. As described above, in the ligament graft-securing device 10, an angle is formed between the screw securing hole-forming part 12 and the flat plate part 11 along the bone to which the ligament graft is to be secured. Thus, the ligament graft penetration spikes 13 and the temporarily securing spikes 14a and 14b form the angle (θ) with the surface of the screw securing hole-forming part 12.

The ligament graft penetration spikes 13 penetrate through the end of the ligament graft and serves as a means for securing the ligament graft to the bone, in cooperation with the flat plate part 11. Each graft penetration spike 13 is constructed of a front end part 131 and a base part 132, as shown in FIGS. 5 and 6. The diameter of the ligament graft penetration spike 13 is set smaller than that of each of the temporarily securing spikes 14a and 14b (which will be described later) to allow the ligament graft penetration spike 13 to easily penetrate the ligament graft.

It is preferable that the front end part 131 of each spikes 13 is pointed so that it can pierce both the ligament graft and the bone easily. For example, favorably, the front end part 131 is conic, triangular pyramidal or the like and more favorably conic. It is favorable that the front end part 131 has an outer diameter of 1–2 mm and more favorable that it has an outer diameter of 1.1–1.4 mm. It is favorable that the front end part 131 has a length of 6–10 mm and more favorable that it has a length of 7–9 mm. It is preferable that the base part 132 of each spikes 13 is in the shape of a column, a trigonal prism, a square pole. It is preferable that the base part 132 has a diameter of 1–2 mm and a length of 8–15 mm when it is columnar. The ligament graft-securing device 10 has a plurality of the ligament graft penetration spikes 13 each having a comparatively small diameter. In the embodiment, seven graft penetration spikes 13 are formed. It is possible to secure the ligament graft to the bone reliably by forming many graft penetration spikes 13 having a small diameter, respectively. Favorably, the number of the ligament graft penetration spikes 13 is 5–15 and more favorably 7–11. It is preferable that the ligament graft penetration spikes 13 are arranged radially to allow a force to be applied uniformly to the end of the ligament graft.

The temporarily securing spikes 14a and 14b are used to temporarily fix the ligament graft-securing device 10 to the bone. As shown in FIGS. 5 and 6, each of the temporarily securing spikes 14a and 14b is constructed of a front end part 141 and a base part 142. It is preferable that the front end part 141 is pointed so that it can pierce the bone easily. Although it is favorable that the front end part 141 is conic, triangular pyramidal or the like, it is more favorable that the front end part 141 is conic. When the front end part 141 is conic, it is preferable that the angle at the front end of a circular cone is 45–75°. It is preferable that the front end part 141 has a diameter of 1–3 mm and a length of 1–3 mm. It is preferable that the base part 142 is in the shape of a column, a trigonal prism, a square pole or the like. It is preferable that the base part 142 has a diameter of 1–3 mm and a length of 8–15 mm when it is columnar. As in the case of the spikes 8a and 8b of the ligament graft-securing device 1, the part of the temporarily securing spikes 14a and 14b which is to be located at the side of the bone tunnel is flat. It is favorable that the temporarily securing spikes 14a and 14b are longer than the ligament graft penetration spike 13 by 1–5 mm and more favorable that the former is longer than the latter by 1–3 mm. The temporarily securing spikes 14a and 14b are formed in the neighborhood of the center of the ligament graft-securing device 10 in its lengthwise direction. The ligament graft penetration spikes 13 are formed at one side (front end side) of the ligament graft-securing device 10.

The temporarily securing spikes 14a and 14b can be arranged as desired, provided that they can secure the ligament graft-securing device 10 to the bone reliably and do not interfere with a screw when the securing of the ligament graft-securing device 10 to the bone is completed by tightening the screw into the screw securing hole 15. For example, as shown in FIG. 4, it is preferable that the temporarily securing spikes 14a and 14b are located near either end of the flat plate part 11 in its lengthwise direction.

As the material of the ligament graft penetration spikes 13 and the temporarily securing spikes 14a and 14b, it is possible to use a material having a necessary degree of strength and adaptable for organisms. For example, it is possible to use stainless steel (SUS304, SUS316, and the like of JISG4303), pure titanium (JISH4670), and a titanium alloy (Ti-6Al-4V, ASTM F-136 Ti-6Al-4V ELI of JISH4657). Of the above materials, a titanium alloy of Ti-6Al-4V is more favorable than the other materials.

The ligament graft penetration spikes 13 and the temporarily securing spikes 14a and 14b may be formed integrally with the flat plate part 11 or separately therefrom. When they are formed separately from the flat plate part 11, the former is connected with the latter by soldering the former to the latter or fitting the former into a hole formed in the latter.

The screw securing hole 15 is used to pass thereinto threads sewed to an end of the ligament graft to apply a desired degree of a tensile force to the ligament graft and continue to apply the tensile force thereto. The screw securing hole 15 is also used to secure thereto the screw used to complete the securing of the ligament graft-securing device 10 to the bone after the ligament graft-securing device 10 is secured thereto temporarily. It is preferable that the screw securing hole 15 is circular because it is used to insert the screw thereinto. Referring to FIG. 6, it is preferable that the screw securing hole 15 is so shaped as to accommodate the screw head therein to prevent the screw head from projecting from the body part of the ligament graft-securing device 10 when the ligament graft-securing device 10 is secured to the bone with the screw. In other wards, the screw securing hole 15 has a screw head receiving portion for receiving the screw head of the screw 91. Thus, it is possible to prevent the inner surface of the skin from being damaged by the screw head. As shown in FIG. 4, it is preferable that the periphery of the screw securing hole 15 is rounded to prevent the periphery from easily damaging the sewing thread sewed to the end of the ligament graft. It is favorable that the screw securing hole 15 has a diameter of 3–8 mm and more favorable that it has a diameter of 4–7 mm. It is favorable that the screw head has a diameter of 4–9 mm, preferably 5–9 mm and more favorable that it has a diameter of 7 mm.

A ligament graft-securing device according to still another embodiment of the present invention will be described below.

Figure 7:
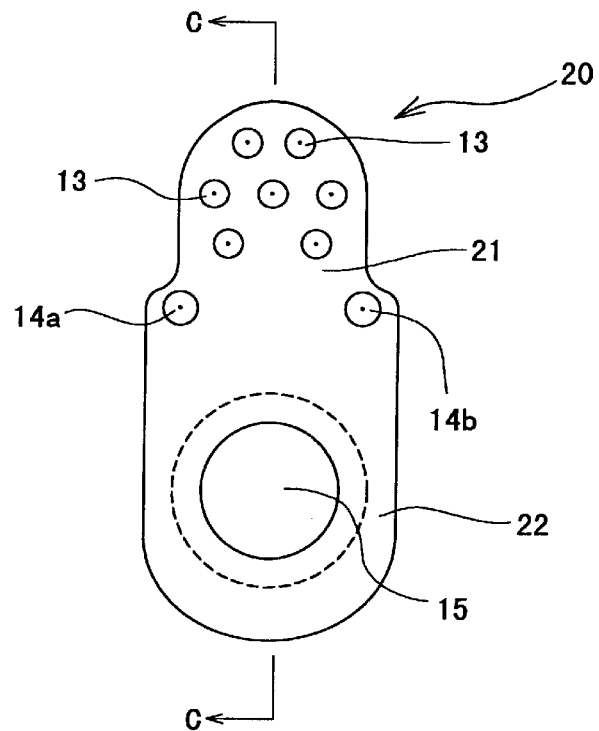
FIG. 7 is a plain view showing the ligament graft-securing device 3 according to still another embodiment of the present invention.
Figure 8:
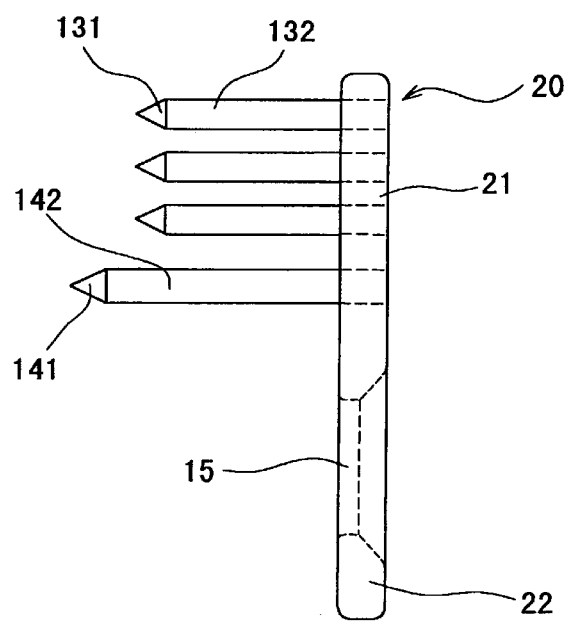
FIG. 8 is a side view showing the ligament graft-securing device shown in FIG. 7.
Figure 9:
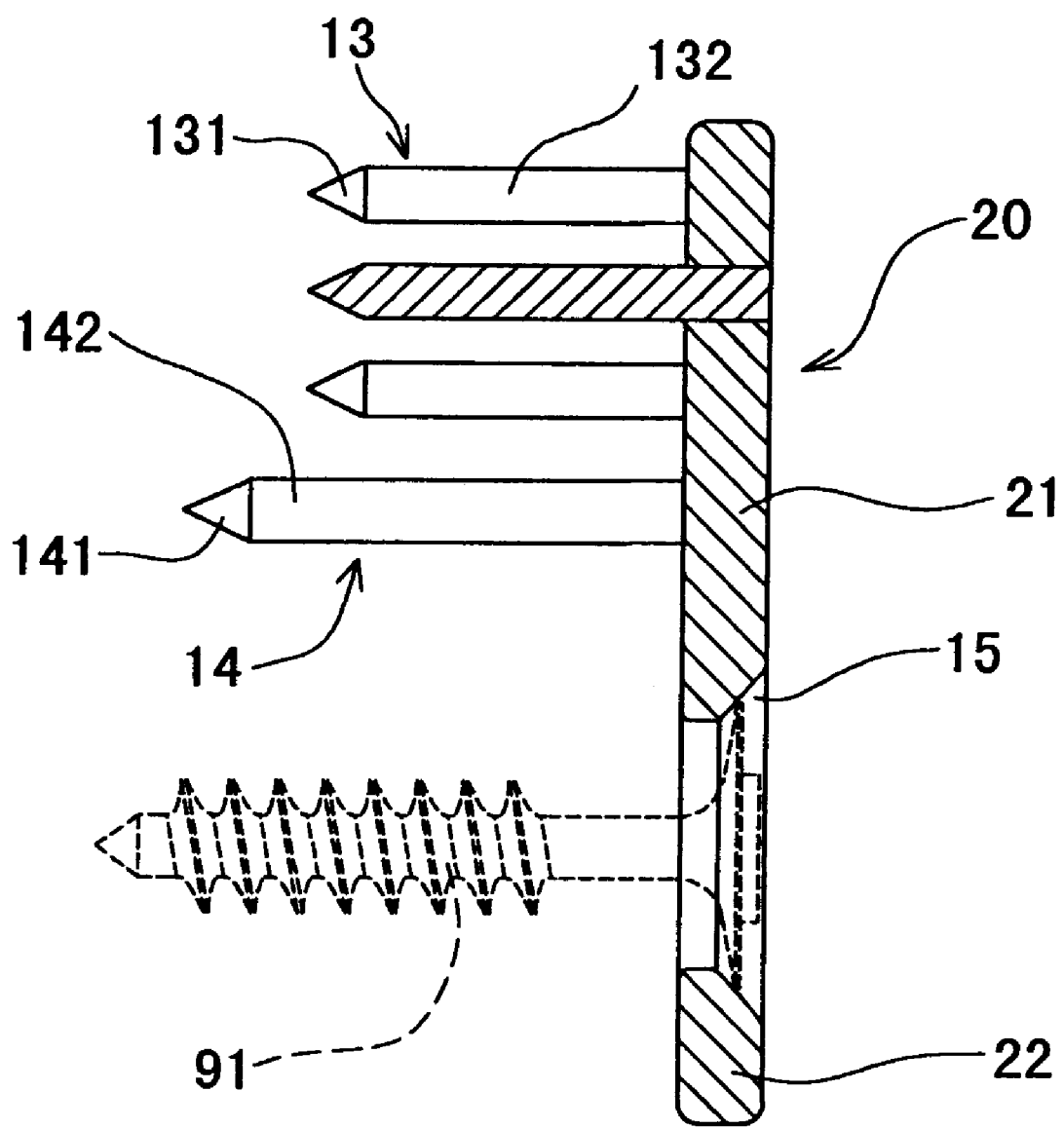
FIG. 9 is a sectional view showing the ligament graft-securing device shown in FIG. 7 taken along the line C—C.

FIG. 7 is a plain view showing a ligament graft-securing device according to still another embodiment of the present invention. FIG. 8 is a side view showing the ligament graft-securing device shown in FIG. 7. FIG. 9 is a sectional view showing the ligament graft-securing device shown in FIG. 7 taken along a line C—C of FIG. 7.

Similarly to the ligament graft-securing device 10, a ligament graft-securing device 20 of this embodiment is used to secure a ligament graft having a length projecting from an end of a bone tunnel formed in a region to which the ligament graft is to be secured.

The ligament graft-securing device 20 includes a screw securing hole-forming part 22 having a screw securing hole 15 through which threads sewed to an end of the ligament graft is passed and which is used to secure the ligament graft-securing device 20 to a bone; a flat plate part 21 located nearer to the side of the bone tunnel than the screw securing hole-forming part 22; a plurality of graft penetration spikes 13 projecting substantially perpendicularly from the flat plate part 21; and temporarily securing spikes 14a and 14b for temporarily securing the ligament graft-securing device 10 to the bone and which are formed on a periphery of the flat plate part 21 such that the from the flat plate part 21 in substantially parallel with the ligament graft penetration spikes 13 and in the same direction as the direction in which the ligament graft penetration spikes 13 project.

The ligament graft-securing device 20 is different from the ligament graft-securing device 10 in that the screw securing hole-forming part 22 and the flat plate part 21 do not form an angle therebetween but are in a straight line, as shown in FIGS. 8 and 9. Thus, like parts are denoted by like reference numerals and descriptions thereof are omitted herein. Because the screw securing hole-forming part 22 and the flat plate part 21 are in a straight line, the ligament graft penetration spikes 13 and the temporarily securing spikes 14a and 14b are substantially perpendicular to the surface of the screw securing hole-forming part 22.

The ligament graft-securing devices 1 and 10 are used mainly in an operation of reconstructing anterior or posterior cruciate ligaments of joints of knee.

A patient is placed in a supine position under a general anesthesia. Using a leg holder, the knee joint is bent at 75–80°, with the lower limb drooped by gravity. A longitudinal skin incision of 3–4 cm is made medial to the tibial tuberosity. A ligament graft consisting of four hamstring tendons is prepared by one of the following methods. The insertion of the semitendinosus muscle attaching to the tibia is dissected, and the semitendinosus tendon is harvested with a tendon stripper. The harvested semitendinosus tendon is folded in four to prepare a ligament graft of 7–9 mm in diameter and of 6 cm or more in length. Threads are sewed to both ends of the ligament graft (short graft=30 in FIG. 10). The insertion of the semitendinosus muscle attaching to the tibia and the insertion of gracilis muscle attaching thereto are dissected. The semitendinosus and the gracilis tendons are harvested respectively. The harvested semitendinosus and gracilis tendons are folded in two respectively to prepare a ligament graft of 7–9 mm in diameter and of 8 cm or more in length. Threads are sewed to both ends of the ligament graft (long graft=50 in FIG. 11).

Figure 11:
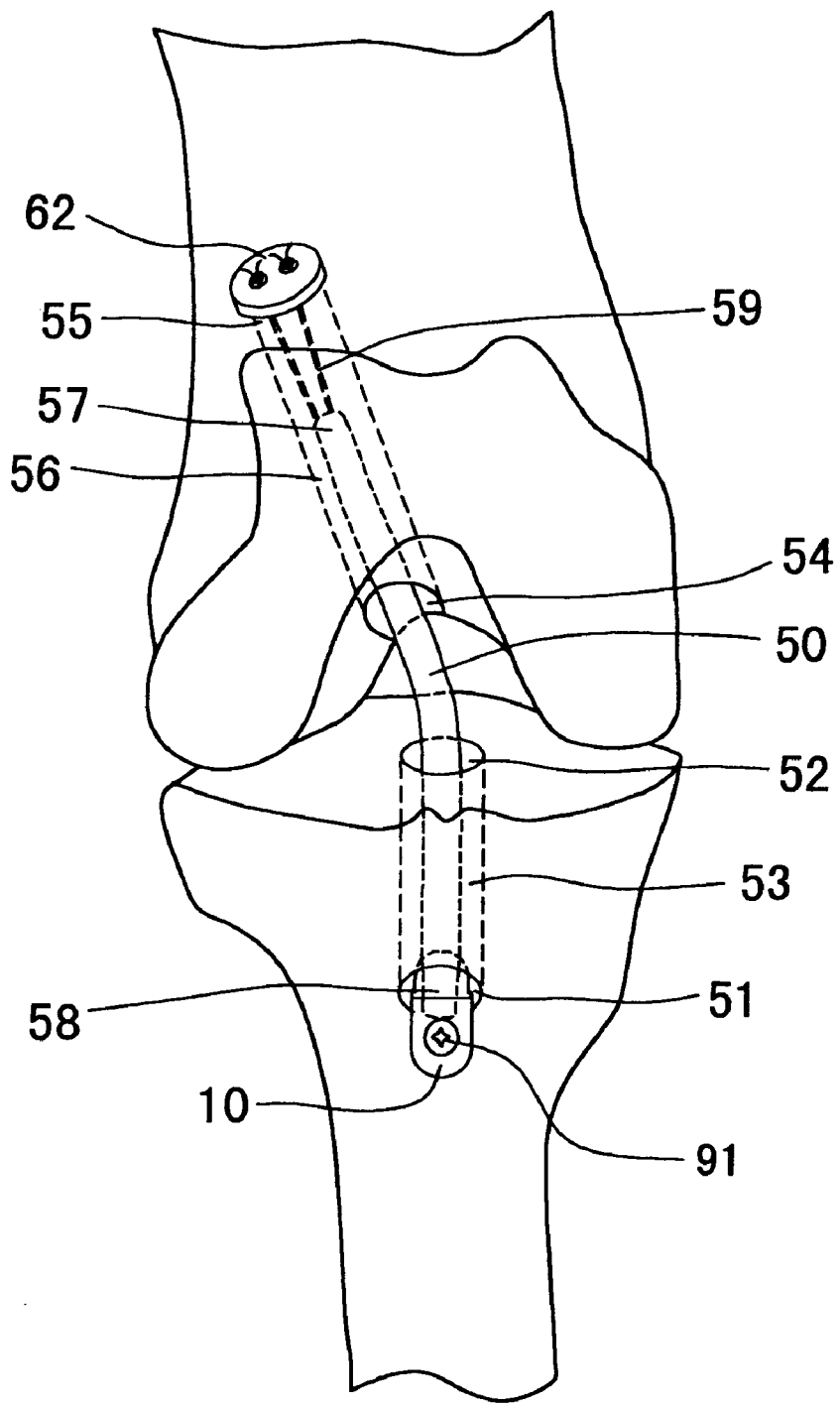
FIG. 11 is an explanatory view for explaining the operation of a ligament graft-securing device according to another embodiment of the present invention.

As shown in FIGS. 10 and 11, using a guide, a tibial bone tunnel 33 or 53 of 7–9 mm in diameter is created in the tibia from the point 31 or 51 medial to the tibial tuberosity to the center 32 or 52 of the tibial attachment of the anterior cruciate ligament.

Then, through the tibial bone tunnel 33 or 53, a femoral bone tunnel 36 or 56 of 7–9 mm in diameter is created from the portion 34 or 54 of the femoral attachment of the anterior crucial ligament to the outer cortex 35 or 55 of the femur. A thread 39 or 59 sewed to an end 37 of the ligament graft 30 or to an end 57 of the ligament graft 50 is guided from the tibia bone tunnel 33 or 53 into the knee joint and guided to the outer cortex 35 or 55 of the femur through the femur bone tunnel 36 or 56. After 1.5 cm or more of the end 37 or 57 of the ligament graft 30 or 50 is introduced into the femoral bone tunnel 36 or 56, using a button 42 or 62, the ligament graft 30 or 50 at its femoral side is secured to the femur on the outer cortex 35 or 55 thereof by pull-out method.

When the ligament graft is short, the ligament graft-securing device 1 is used. A sewing thread 40 sewed to an end 38 of the ligament graft 30 is tied through the knotting hole 5, as shown in FIGS. 1 and 10. Then, a tensile force is applied in a desired degree to the thread 40 secured to the through-hole 7. The spikes 8a and 8b are tapped into the bone, with the application of the tensile force to the thread 40 maintained. At the last stage, the screw 90 is driven into the screw securing hole 6 to secure the ligament graft-securing device 1 to the bone.

When the ligament graft is long, as shown in FIGS. 4 and 11, threads sewed to an end 58 of the ligament graft 50 are divided into two. Then, a tensile force at a necessary degree is applied to each thread. The temporarily securing spikes 14a and 14b are pierced into the bone perpendicularly to the ligament graft 50 in penetration therethrough, with the application of the tensile force to the sewing thread maintained. The screw 91 is tightened into the screw securing hole 15 to complete the securing of the ligament graft-securing device 10 to the bone.

The method of performing an operation of repairing the inner-side collateral ligament to be carried out by using the ligament graft-securing device 20 is described below with reference to FIGS. 7 and 12.

A patient is placed in a supine position under a general anesthetic. Using a lower limb-holding device, the joint of knee is bent at 75–80°, with the lower limb and the region lower than the lower limb descending. The skin is longitudinally cut in a length of 9–11 cm at the inner side of the joint of knee. The semitendinosus muscle tendon is collected with the tendon separator. The collected semitendinosus muscle tendon is folded in two to prepare a ligament graft 70 having a diameter of 5–7 mm and a length of 12 cm or more. A sewing thread is sewed to both ends of the ligament graft 70. A hole 73 having a diameter of 5–7 mm is formed with a drill in a region from a portion 71 of the inner-side collateral ligament attaching to the femur to an outer cortex 72 of the femur. After 1.5–2.5 cm of one end 74 of the ligament graft 70 is introduced into the hole 73, a sewing thread 75 is taken out from the hole 73 onto the outer cortex 72 of the femur. Then, using a button 76, the ligament graft 70 at its femur side is secured to the femur by the pull-out method.

Figure 12:
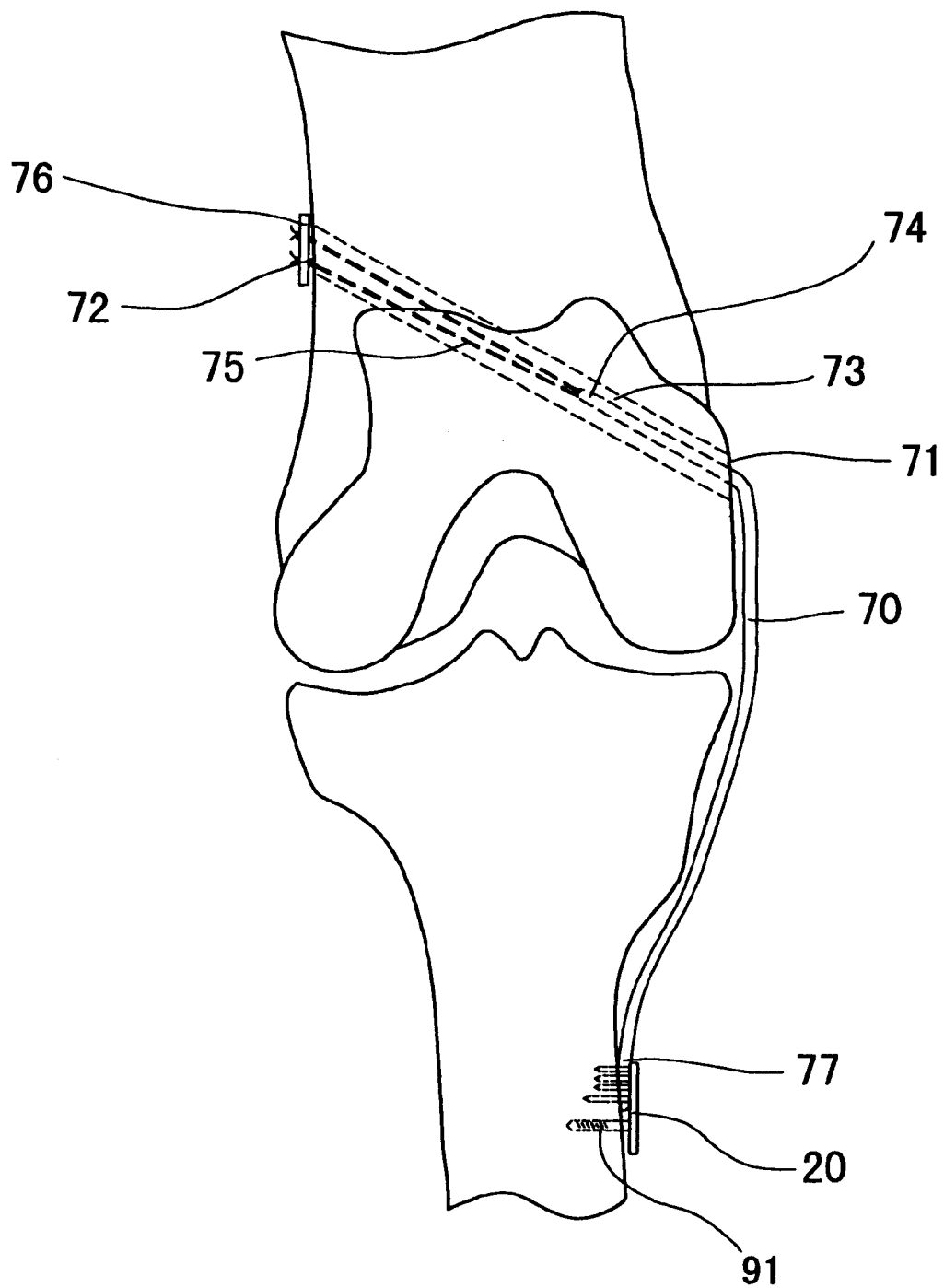
FIG. 12 is an explanatory view for explaining the operation of a ligament graft-securing device according to still another embodiment of the present invention.

Then, as shown in FIGS. 7 and 12, a tensile force is applied at a necessary degree to a thread sewed to the other end 77 of the ligament graft 70. The ligament graft penetration spikes 13 and the temporarily securing spikes 14a and 14b are tapped into the bone perpendicularly to the ligament graft 70 in penetration therethrough. A screw 92 is driven into the screw securing hole 15 to complete the securing of the ligament graft-securing device 20 to the bone. The ligament graft-securing device 20 is used by curving it appropriately according to the configuration of the bone. It is possible to use the pull-out method at the tibial side and the ligament graft-securing device 20 at the femoral side in securing the ligament graft.

Figure 13:
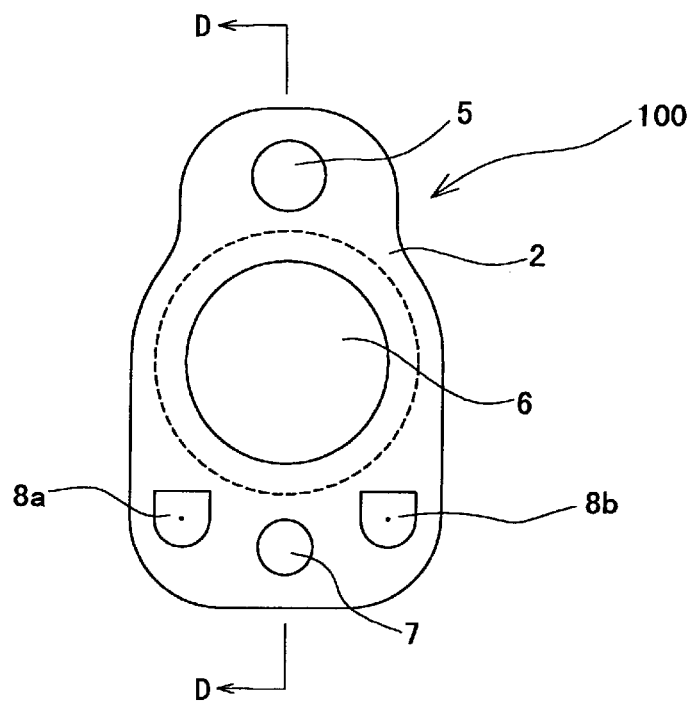
FIG. 13 is a plain view showing a ligament graft-securing device according to still another embodiment of the present invention.

A graft-securing device 100 will be described below with reference to FIGS. 13 though 15.

Figure 2:
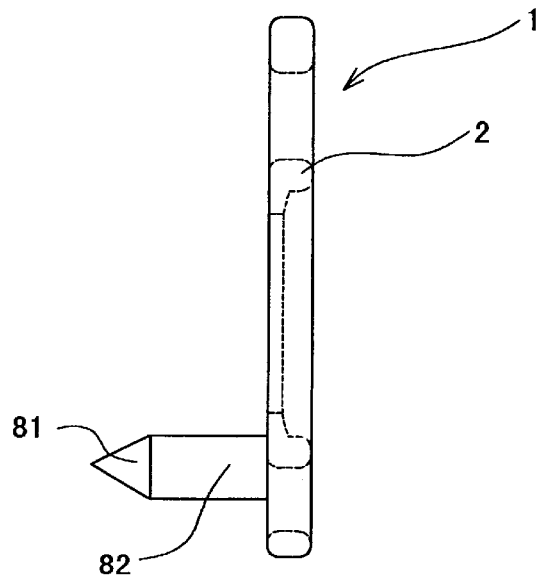
FIG. 2 is a side view showing the ligament graft-securing device shown in FIG. 1.
Figure 3:
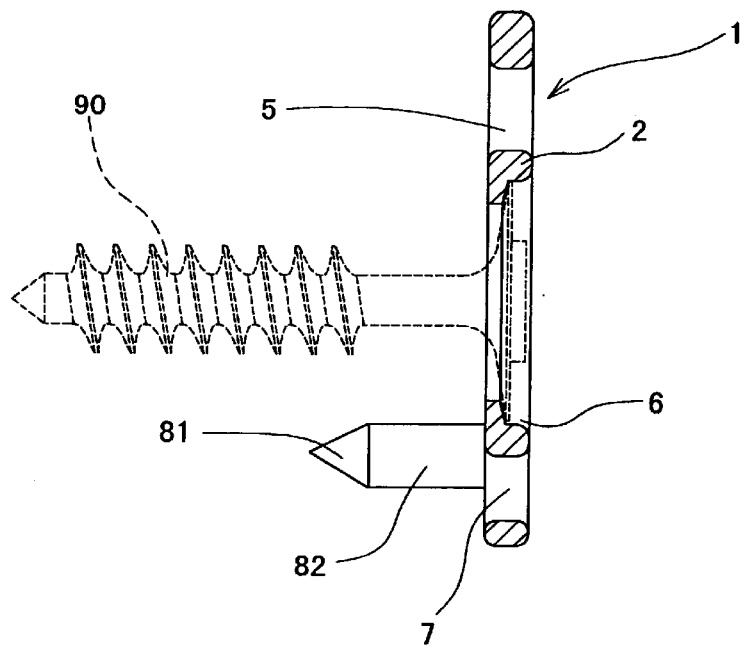
FIG. 3 is a sectional view showing the ligament graft-securing device shown in FIG. 1 taken along the line A—A.
Figure 14:
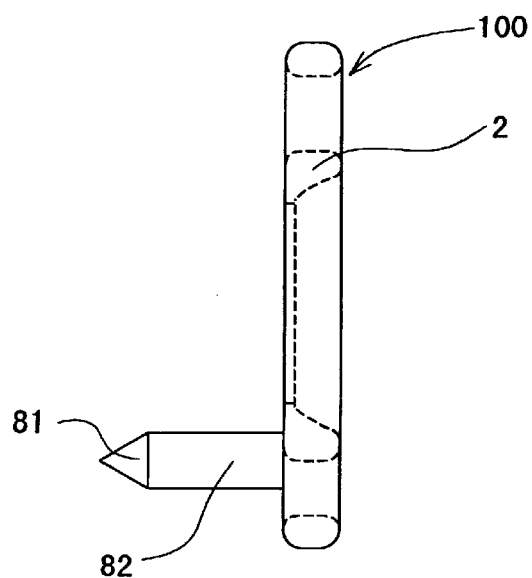
FIG. 14 is a side view showing the ligament graft-securing device shown in FIG. 13.
Figure 15:
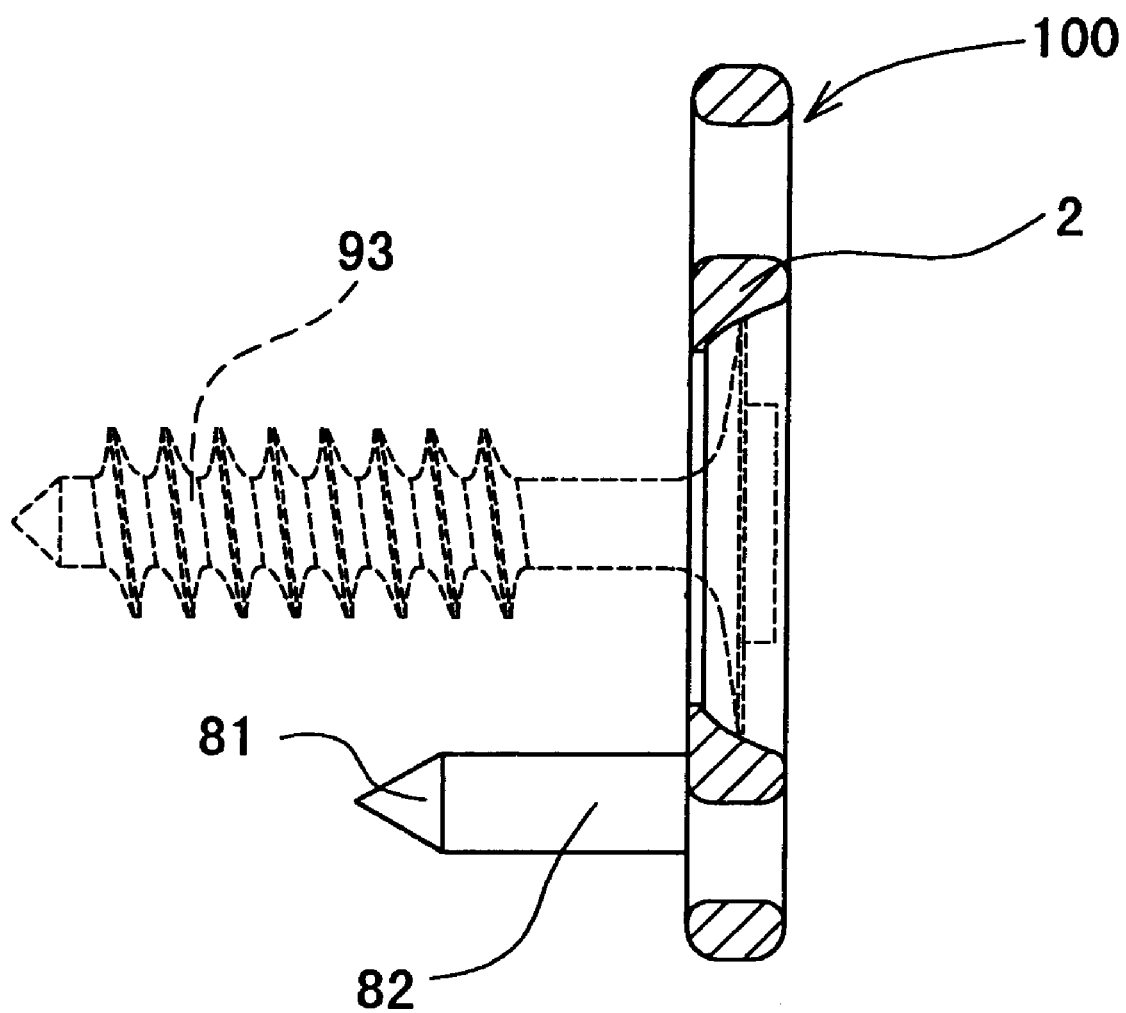
FIG. 15 is a sectional view showing the ligament graft-securing device shown in FIG. 14 taken along the line D—D.

The basic composition of the ligament graft-securing device 100 is same to the ligament graft-securing device 1 which was illustrated on FIGS. 1 to 3 and was explained. Size and a shape of a peripheral portion of a screw securing hole 6 are as for a difference of the ligament graft-securing device 100 and the ligament graft-securing device 1. The peripheral portion of the screw securing hole 6 is tapered so that the inner diameter becomes gradually smaller to a distal end of spikes 8a and 8b as shown in FIGS. 13 to 15. The screw securing hole 6 has a screw head receiving portion for receiving a screw head of a screw 83 as shown in FIG. 15.

Two pieces of the ligament graft-securing device 100 are spiked on a opening of the tibial bone tunnel 33. For this reason, the ligament graft-securing device 100 is smaller than the ligament graft-securing device 1.

The ligament graft-securing device 1 has a thickness of 1–3 mm and a length of 8–18 mm, preferably 9–16 mm, a width of 3–7 mm and a length of 3–6 mm in one side (at the part where the suture hole 5 is formed) thereof; and a width of 6–10 mm in the part where the screw securing hole 6 is formed and in the part where the through-hole 7 is formed.

The ligament graft-securing device 100 is used mainly in an operation of reconstructing anterior or posterior cruciate ligaments of joints of knee.

A patient is placed in a supine position under a general anesthesia. Using a leg holder, the knee joint is bent at 75–80°, with the lower limb drooped by gravity. A longitudinal skin incision of 3–4 cm is made medial to the tibial tuberosity. A graft consisting of four hamstring tendons is prepared by one of the following methods. The insertion of the semitendinosus muscle attaching to the tibia is dissected, and the semitendinosus tendon is harvested with a tendon stripper. The harvseted semitendinosus tendon is divided into 2 pieces. Each divided tendons are folded in four to prepare two grafts of 4–7 mm in diameter and of 6 cm or more in length. Threads are sewed to both ends of the ligament graft (short grafts=30a, 30b in FIG. 16).

Figure 16:
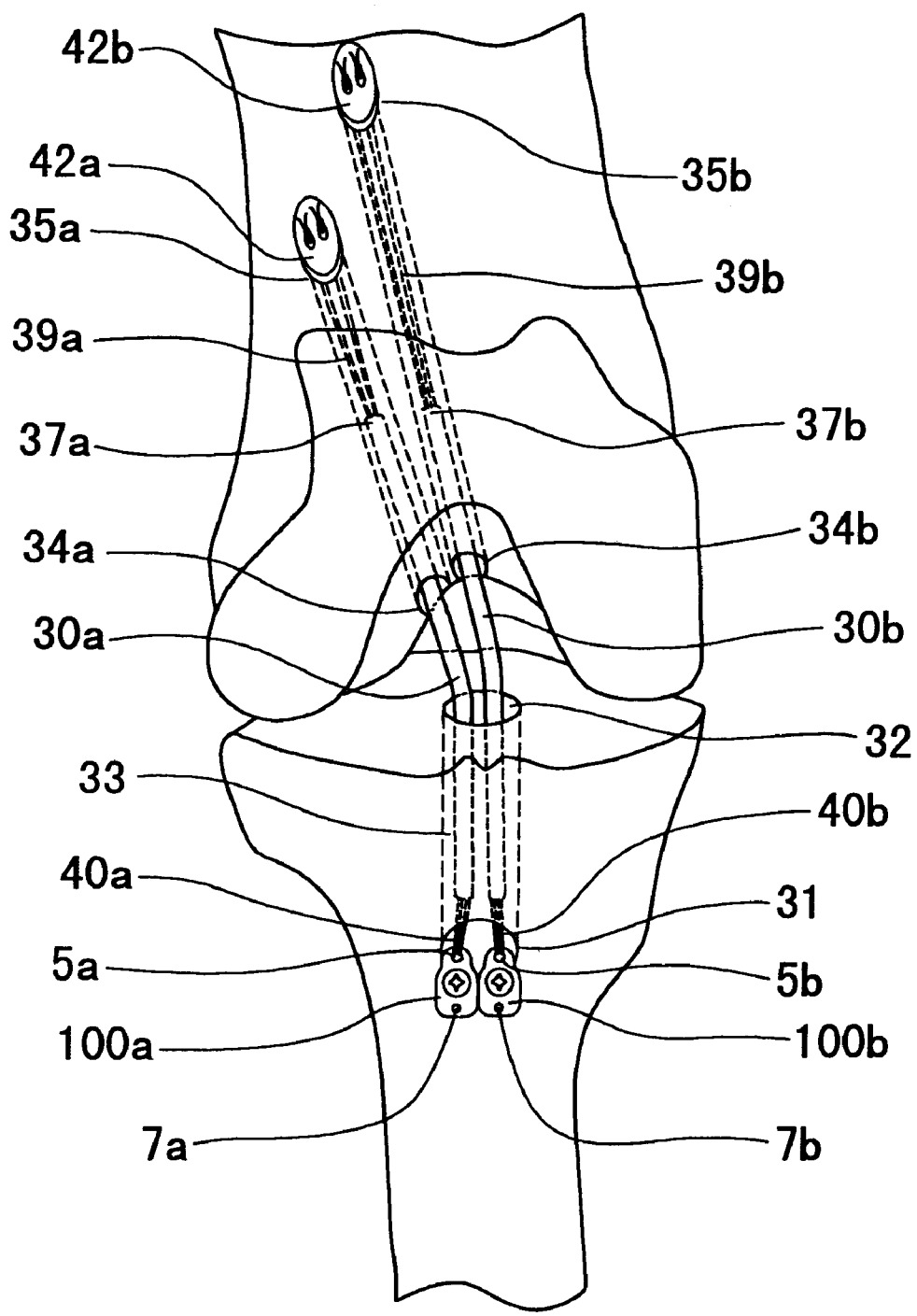
FIG. 16 is an explanatory view for explaining the operation of a ligament graft-securing device according to still another embodiment of the present invention.

As shown in FIG. 16, using a guide, a tibial bone tunnel 33 of 7–9 mm in diameter is created in the tibia from the point 31 medial to the tibial tuberosity to the center 32 of the tibial attachment of the anterior cruciate ligament. Then, through the tibial bone tunnel 33, two femoral bone tunnela 36a and 36b of 4–7 mm in diameter is created from the portions 34a, 34b of the femoral attachment of the anterior crucial ligament to the outer cortexes 35a, 35b of the femur. Threads 39a, 39b sewed to ends 37a, 37b of the ligament grafts 30_a_, 30_b_ are guided from each tibia bone tunnels 33_a_, 33_b_ into the knee joint and guided to the outer cortexes 35_a_, 35_b_ of the femur through the femur bone tunnels 36_a_, 36_b_. After 1.5 cm or more of the ends 37_a_, 37_b_ of the ligament grafts 30_a_, 30_b_ are introduced into the corresponding femoral bone tunnels 36_a_, 36_b_, using buttons 42_a_, 42_b_, the ligament grafts 30_a_, 30_b_ at femoral side thereof are secured to the femur on the outer cortexes 35_a_, 35_b_ thereof by pull-out method. Sewing threads 40_a_, 40_b_ sewed to ends 38_a_, 38_b_ of the ligament grafts 30_a_, 30_b_ are tied through the corresponding knotting holes 5_a_, 5_b_, as shown in FIG. 16. Then, a tensile force is applied in a desired degree to the threads 40_a_, 40_b_ secured to the through-holes 7_a_, 7_b_. The spikes 8_a_ and 8_b_ are tapped into the bone, with the application of the tensile force to the threads 40_a_, 40_b_ maintained. At the last stage, screws 93_a_, 93_b_ are driven into the screw securing holes 6_a_, 6_b_ to secure the ligament graft-securing device 100_a_, 100_b_ to the bone.

The ligament graft-securing device of the present invention is used to secure to a bone a ligament graft having a length not projecting from a bone tunnel exit formed in a region to which the ligament graft is to be secured. The ligament graft-securing device includes a body part; a knotting hole formed at one end of the body part to knot therein threads sewed to an end of the ligament graft; a through-hole formed at the other end of the body part to secure a tensile force-applying thread thereto; spikes projecting from one surface of the body part to temporarily fix the ligament graft-securing device to a bone; and a screw securing hole formed on the body part to secure the ligament graft-securing device to the bone.

In the construction, in securing one end of the short graft not projecting from the bone tunnel to the bone, a thread sewed to one end of the ligament graft is tied in the knotting hole, and a tensile force-applying thread secured in the through-hole is pulled to apply a tensile force in a desired extent to the ligament graft. In this state, the ligament graft is driven with a device to temporarily fix the one end of the ligament graft to the bone easily. Then, a screw is used to complete the securing of the one end of the ligament graft to the bone. Thus, it is possible to secure the one end of the ligament graft to the bone firmly, easily, and in a short period of time, with a desired degree of the tensile force being applied to the ligament graft.

Another graft-securing device of the embodiment of the present invention is used to secure a bone a ligament graft having a length projecting from a bone tunnel exit formed in a region to which the ligament graft is to be secured. The ligament graft-securing device includes a screw securing hole-forming part having a screw securing hole through which threads sewed to an end of the ligament graft is inserted and which is used to secure the ligament graft-securing device to a bone; a flat plate part located closer to a bone tunnel than the screw securing hole-forming part; a plurality of graft penetration spikes projecting substantially perpendicularly from the flat plate part; and temporarily securing spikes which are formed on a periphery of the flat plate part such that they project from the flat plate part in substantially parallel with the ligament graft penetration spikes and in the same direction as the direction in which the ligament graft penetration spikes project and which are used to temporarily secure the ligament graft-securing device to the bone.

In the construction, in securing one end of the long graft projecting from the bone tunnel to the bone, a sewing thread sewed to the one end of the ligament graft is pulled to apply a desired degree of a tensile force to the ligament graft. In this state, the ligament graft is driven to temporarily fix the one end of the ligament graft to the bone easily. Then, a screw is used to complete the securing of the one end of the ligament graft to the bone. Thus, it is possible to secure the one end of the ligament graft to the bone firmly, easily, and in a short period of time, with a desired degree of the tensile force being applied to the ligament graft. Further, according to the present invention, it is possible to secure the one end of the ligament graft inside the bone tunnel without causing a patient to have ache, unlike the conventional method of securing an end of a ligament graft to the outer surface of the bone. In the conventional securing method, the ligament graft and the ligament graft-securing device are superimposed on each other, thus projecting greatly to the skin and causing patients' ache.

What is claimed is:

1. A ligament graft-securing device for securing a ligament graft having a length not projecting from a bone tunnel formed in a region to which said graft is to be secured, comprising:

a body part;

a knotting hole for knotting therein a thread sewed to an end of said graft and which is formed at one end of said body part;

a through-hole for securing a tensile force-applying thread thereto and which is formed at the other end of said body part;

a spike for temporarily fixing said graft-securing device to a bone and which projects from one surface of said body part; and a screw securing hole for securing said graft-securing device to said bone and which is formed on said body part.

2. A ligament graft-securing device according to claim 1, wherein said ligament graft-securing device has two spikes for temporarily fixing said graft-securing device to a bone, one of which is formed at one side of said body part and the other of which is formed at the other side thereof.

3. A ligament graft-securing device according to claim 2, wherein said spikes are formed at the other side of said body part and said spikes are parallel with each other and substantially perpendicular to said body part.

4. A ligament graft-securing device according to claim 2, wherein said through-hole is arranged near or in a middle part of two spikes.

5. A ligament graft-securing device according to claim 1, wherein said screw securing hole is formed between said knotting hole and said through-hole.

6. A ligament graft-securing device according to claim 1, wherein said screw securing hole has a screw head receiving portion for receiving a screw head of a screw.

7. A ligament graft-securing device for securing a ligament graft having a length projecting from a bone tunnel formed in a region to which said graft is to be secured, comprising:

a screw securing hole-forming part having a screw securing hole through which a thread sewed to an end of said graft is inserted and which is used to secure said graft-securing device to a bone and;

a flat plate part;

a plurality of ligament penetration spikes projecting substantially perpendicularly from said flat plate part; and a plurality of temporarily securing spikes for temporarily securing said graft-securing device to the bone and which are formed on a periphery of said flat plate part such that said temporarily securing spikes project from said flat plate part in substantially parallel with said ligament penetration spikes and in the same direction as that in which said ligament penetration spikes project.

8. A ligament graft-securing device according to claim 7, wherein said screw securing hole-forming part and said flat plate part form a certain angle therebetween.

9. A ligament graft-securing device according to claim 7, wherein said screw securing hole-forming part and said flat plate part are substantially on the same plane.

10. A ligament graft-securing device according to claim 7, wherein the number of said temporarily securing spikes is two, one of which is formed at one side of said flat plate part and the other of which is formed at the other side thereof.

11. A ligament graft-securing device according to claim 7, wherein said temporarily securing spikes are longer than any of said ligament penetration spikes.

12. A ligament graft-securing device according to claim 7, wherein said screw securing hole has a screw head receiving portion for receiving a screw head of a screw.

* * * * *